US012751473B2

(12) United States Patent
Ong

(10) Patent No.: US 12,751,473 B2
(45) Date of Patent: Oct. 6, 2026

(54) MEAT FLAVOURING

(71) Applicant: ANTS INNOVATE PTE. LTD., Singapore (SG)

(72) Inventor: Shujian Ong, Singapore (SG)

(73) Assignee: ANTS INNOVATE PTE. LTD., Singapore (SG)

( * ) Notice: Subject to any disclaimer, the term of this patent is extended or adjusted under 35 U.S.C. 154(b) by 344 days.

(21) Appl. No.: 18/254,827

(22) PCT Filed: Nov. 30, 2021

(86) PCT No.: PCT/EP2021/083526
§ 371 (c)(1),
(2) Date: May 26, 2023

(87) PCT Pub. No.: WO2022/112593
PCT Pub. Date: Jun. 2, 2022

(65) Prior Publication Data

US 2024/0306685 A1 Sep. 19, 2024

(30) Foreign Application Priority Data

Nov. 30, 2020 (SG) ........................... 10202011940U

(51) Int. Cl.
*A23L 27/26* (2016.01)
*A23J 3/22* (2006.01)
*A23L 27/21* (2016.01)
*C12N 5/077* (2010.01)

(52) U.S. Cl.
CPC ............... *A23L 27/26* (2016.08); *A23J 3/227* (2013.01); *A23L 27/215* (2016.08); *C12N 5/0656* (2013.01); *C12N 5/0658* (2013.01)

(58) Field of Classification Search
CPC ........ A23L 27/26; A23L 27/215; A23J 3/227; C12N 5/0656; C12N 5/0658
USPC .......................................................... 426/533
See application file for complete search history.

(56) References Cited

U.S. PATENT DOCUMENTS

| | | | | |
|---|---|---|---|---|
| 6,495,184 | B1 | 12/2002 | Zheng et al. | |
| 9,332,779 | B2 | 5/2016 | Marga | |
| 2016/0213037 | A1 | 7/2016 | Groenewold | |
| 2020/0100525 | A1* | 4/2020 | Savir | A23L 13/65 |
| 2024/0148024 | A1* | 5/2024 | Ong | A23J 3/26 |

FOREIGN PATENT DOCUMENTS

| | | | |
|---|---|---|---|
| CN | 110730615 | A | 1/2020 |
| WO | 2022/112593 | A1 | 6/2022 |

OTHER PUBLICATIONS

Tomiyama et al., "Bridging the gap between the science of cultured meat and public perceptions" Trends in Food Science & Technology 104:144-152 (2020).

(Continued)

*Primary Examiner* — Brent T O'Hern
(74) *Attorney, Agent, or Firm* — HAMILTON, BROOK, SMITH & REYNOLDS, P.C.

(57) ABSTRACT

This invention relates to the extraction of meat-specific flavour compounds from in vitro cultured animal cells of a meat species by heating the cells in fat, such as plant oil. Meat flavourings and methods of production are provided, along with methods of flavouring foodstuffs, such as meat substitute products, and foodstuffs flavoured by these methods.

10 Claims, 11 Drawing Sheets

(56) References Cited

OTHER PUBLICATIONS

International Search Report for International Application No. PCT/EP2021/083526, entitled "Meat Flavouring," dated Mar. 7, 2022.
Aschemann-Witzel, J. et al., Plant-based food and protein trend from a business perspective: markets, consumers, and the challenges and opportunities in the future, Critical Reviews in Food Science and Nutrition (2020), 1-10.
Ben-Arye, T. & S. Levenberg, Tissue Engineering for Clean Meat Production, Frontiers in Sustainable Food Systems (2019), 1-19, 3:46, https://www.frontiersin.org/article/10.3389/fsufs.2019.00046.
Ben-Arye, T. et al., Textured soy protein scaffolds enable the generation of three-dimensional bovine skeletal muscle tissue for cell-based meat, Nature Food (2020), 210-220, 1 (4).
Datar, I. & M. Betti, Possibilities for an in vitro meat production system, Innovative Food Science and Emerging Technologies (2010), 13-22, 11 (1).
Ding, S. et al., Characterization and isolation of highly purified porcine satellite cells, Cell Death Discovery (2017), 17003-17003, 3.
Intarapat, S., Isolation and characterisation of chick embryonic primordial germ cells, PhD thesis, University College London, London (2017), https://discovery.ucl.ac.uk/id/eprint/1344049.
Maughan, C. & S. Martini, Identification and quantification of flavor attributes present in chicken, lamb, pork, beef, and turkey, Journal of food science (2012), S115-21, 77,2.
Ong, S. et al., Cell-based meat: Current ambiguities with nomenclature, Trends in Food Science & Technology (2020), 223-231, 102.
Public Health England, Determination of water activity in food, National Infection Service. Food, Water & Environmental Microbiology Standard Method FNES67 Version 2 (2017).
Schindelin, J. et al., Fiji: an open-source platform for biological-image analysis, Nat Meth (2012), 676-682, 9(7), http://dx.doi.org/10.1038/nmeth.2019.
Specht, L., An analysis of culture medium costs and production vols. for cell-based meat, The Good Food Institute: Washington, DC, USA (2020).
Sushant Aryal et al., Total Phenolic Content, Flavonoid Content and Antioxidant Potential of Wild Vegetables from Western Nepal, Plants (2019), 1-12, 8(4).
Badawy et al., "Conjugated linoleic acid (CLA) as a functional food: Is it beneficial or not?" Food Research International, 172, 2023, 113158, 1-26.

* cited by examiner

MEAT FLAVOURING

RELATED APPLICATIONS

This application is the U.S. National Stage of International Application No. PCT/EP2021/083526, filed Nov. 30, 2021, which designates the U.S., published in English. and claims priority under 35 U.S.C. § 119 or 365 (c) to Singapore Application No. SG10202011940U, filed Nov. 30, 2020. The entire teachings of the above applications are incorporated herein by reference.

FIELD

The present invention relates to meat flavourings, methods for producing meat flavourings and the use of meat flavourings, for example, in the production of meat-substitute foodstuffs.

BACKGROUND

Conventional meat production is known to be harmful to the environment, human health and raises animal ethical concerns (4). Alternatives to meat have attracted significant attention among consumers in recent times. Key market drivers include consumer health consciousness, food safety concerns, food security issues, and concerns for environmental and society (1). Plant-based meat are substitutes to meat made using plant-based proteins like soy and pea protein isolates. Plant-based proteins are textured to recreate meat-like texture and flavoured to imitate umami flavours of meat. These products do not have meat-like aroma.

Cell-based cultured meat is a meat alternative produced by in vitro culture of animal cells (7). Cultured meat production promises to produce real meat with the same taste, texture, nutrition, and appearance of meat, without any live animals. The product is intended to recreate animal meat more accurately than plant-based meats. Most players in the industry focus on developing technology for large-scale and low-cost culture of cells. Cells, which will form a significant portion of the product, are intended to be combined with scaffolds and other ingredients to form meat products. Current cell-based meat products, based on claims, are estimated to cost about US $200 per kg, with bulk of the cost (55-95%) related to culture medium. Another issue is the scalability of animal cell culture, with highest reported densities upwards of $1\times10^8$ viable cells/mL in suspension culture (10). Given the major challenges of high cost of raw materials and the limited scalability of cell culture, the first cell-based meat products are likely to be extremely expensive and limited to a select few consumers.

The current understanding of flavour generation in cell-based meat is nascent. A consensus is that to recreate meats, muscle cells need to be grown and differentiated into muscle fibres to recreate meat muscles and flavours, while adipocytes would need to be grown to recreate animal fats and flavours. Methods for culturing cells and inducing "fattening" or adipogenesis for use in cell-based meat have been reported (3-4). Cells are also proposed to be used as a flavouring ingredient by addition to plant-originated substances at a small quantity without prior processing to form a hybrid meat product (5-6).

Cell-based cultured meat has been heralded as the future of food, requiring no live animals to produce real animal protein. Most players in the field focus on scaling up animal cell culture to produce meat substitutes incorporating at least 20% of cells. Given the major challenges of high cost of raw materials and the limited scalability of cell culture, the first cell-based meat products are likely to be extremely expensive and limited to a select few consumers. The development of low-cost methods for the generation of meat alternatives with better taste than purely plant-based products would be desirable.

SUMMARY

The present inventors have developed a method for extracting meat-specific flavour compounds from in vitro cultured animal cells by heating the cells in fat. This is found to generate a flavouring with a meat aroma and flavour that is reminiscent of animal fats. Meat flavouring produced by this method may be useful as high-value, low-volume source of meat-specific flavours, for example in the production of meat-substitute foodstuffs.

A first aspect of the invention provides a method for producing a meat flavouring comprising;

admixing a population of dried in vitro cultured non-human animal cells with a fat; and heating the admixture, thereby producing the meat flavouring.

A second aspect of the invention provides a meat flavouring produced by a method described herein Meat flavourings of the second aspect may include meat flavoured oils.

A third aspect of the invention provides a method for producing meat flavoured foodstuff comprising;

admixing a meat flavouring of the second aspect with a foodstuff, thereby producing the meat flavoured foodstuff.

A fourth aspect of the invention provides the use of a meat flavouring of the second aspect in the production of a meat flavoured foodstuff.

A fifth aspect of the invention provides a foodstuff comprising a meat flavouring of the second aspect and one or more foodstuff ingredients.

Other aspects and embodiments of the invention are described in more detail below.

DETAILED DESCRIPTION

Figure 1:
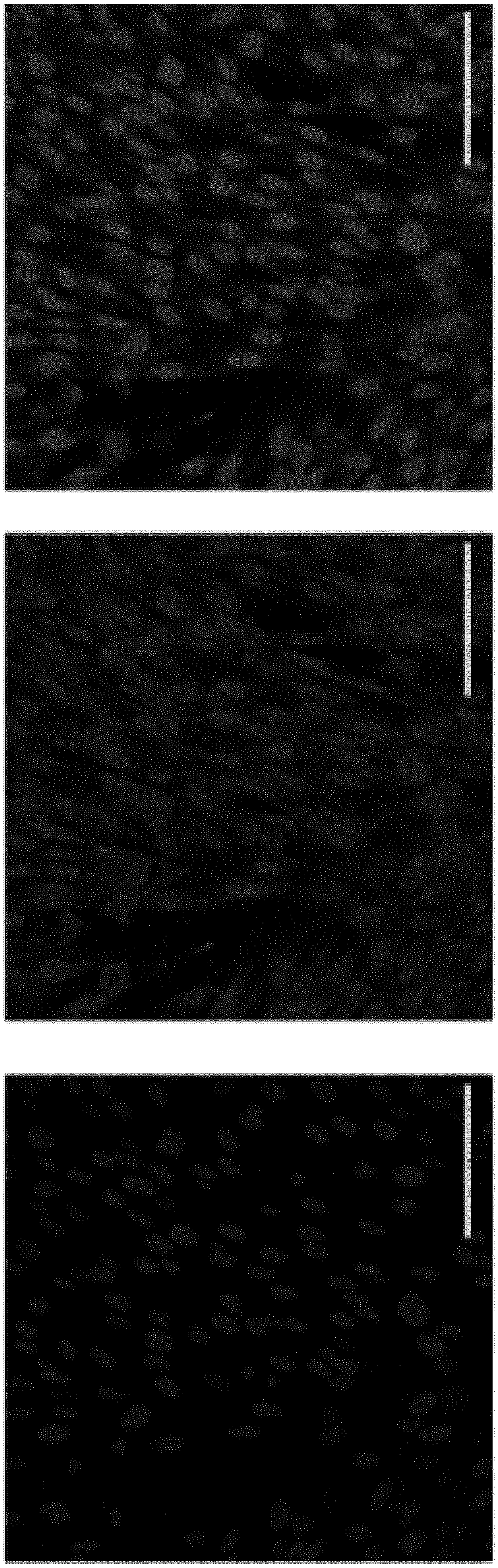
FIG. 1 shows immunofluorescence staining of immortalized porcine myoblasts (IPMs).

The present inventors have surprisingly found that, whilst animal cells or tissue cultured in vitro do not provide meat-specific flavours in a raw untreated form, the heating of in vitro cultured animal cells or tissue in fat generates a favouring with a distinctly strong meaty aroma and flavour reminiscent of animal meats and fats. This allows complex meat-specific flavours to be imparted on foodstuffs that are unattainable with plant-based ingredients.

A meat flavouring, such as a meat flavoured oil, may be produced as described herein by heating animal cells or tissues produced by in vitro cell culture methods in fat. A small quantity of animal cells may be heated to produce the meat flavouring. For example, $10^5$ or more, $10^6$ or more, $10^7$ or more, $10^8$ or more, $10^9$ or more or $10^{10}$ or more cells may be heated. In some embodiments, about $20\times10^6$ cells may be heated.

Animal cells for use in the methods described herein may be non-human animal cells.

The animal cells cultured in vitro may be in the form of single cells or aggregated masses of cells, such as organoids or spheroids. An aggregated mass of animal cells cultured in vitro may be referred to as animal tissue.

In some embodiments, the animal cells may be genetically modified. For example, the cells may comprise exogenous nucleic acid, such as a recombinant vector. In other embodiments, the animal cells may be non-genetically modified. For example, the cells may be devoid of exogenous nucleic acid.

The animal cells may be from a meat species, such as a livestock, poultry or aquatic species. For example, the cultured animal tissue or animal cell may be from cattle, pig, sheep, poultry, duck, deer, rabbit, fish or other seafood. More optionally, the source organism may be selected from a livestock species (such as cow, buffalo, sheep, goat, pig, camel, rabbit, deer, and the like), poultry species (such as chicken, goose, turkey, pheasant, duck, ostrich, and the like), and/or aquatic or semi-aquatic species (such as fish, molluscs (namely, abalone, clam, conch, mussel, oyster, scallop, and snail), cephalopods (namely, cuttlefish, octopus, and squid), crustaceans (namely, crab, crayfish, lobster, prawn, and shrimp), cetaceans, frog, turtles, crocodiles, and the like. In some preferred embodiments, the animal cells may be bovine; porcine; ovine; avian, such as gallinaceous or anatine; cervine; leporine; or piscine cells.

The animal cells confer a distinct species-specific flavour and aroma on the meat flavouring based on the origin of the animal cells. The flavour and aroma of the meat flavouring may be characteristic of the species of the animal cells. For example, bovine cells may be used to generate a beef flavouring, porcine cells may be used to generate a pork flavouring, ovine cells may be used to generate a lamb or mutton flavouring, avian cells may be used to generate a chicken, goose, turkey, pheasant, duck or ostrich flavouring, cervine cells may be used to generate a venison flavouring, leporine cells may be used to generate a rabbit flavouring and piscine cells may be used to generate a fish flavouring.

Flavour and aroma may be assessed or evaluated by any technique known in the art (see for example Maughan et al 2011). For example, flavour and aroma may be evaluated quantitatively on a hedonic scale by a panel of taste testers or using gas chromatography-olfactometry analysis (also known as "e-nose").

The flavour and aroma of a meat flavouring produced as described herein may be further controlled by controlling the cell fate and lineage of the animal cells, thereby producing distinct flavours. For example, the intensity and note of meat-specific flavours may be modulated by the cell fate and lineage of the animal cells used to produce the flavouring.

In some embodiments, the animal cells may be pluripotent, undifferentiated or partly differentiated animal cells. For example, the animal cells may be stem cells. Stem cells are capable of differentiation into different cell fates and lineages including bone cells (osteoclasts, osteoblasts, osteocytes), blood cells (erythrocytes, leukocytes, thrombocytes, macrophages), muscle cells (skeletal and cardiac myoblasts, myocytes, myotubes), connective tissue (fibroblasts), fat cells (adipocytes), nerve cells (neurons), skin cells (epithelial cells, keratinocytes, melanocytes), intestinal cells (endothelial cells), liver cells (hepatocytes). Suitable stem cells include lineage-restricted primary adult progenitor stem cells, or pluripotent stem cells; lineage-restricted immortalized stem cell lines; embryonic stem cells, induced pluripotent stem cells, mesenchymal stem cells or adult stem cells.

In other embodiments, the animal cells may be differentiated animal cells. Differentiated animal cells may exhibit a stronger meat flavour than undifferentiated cells and may be preferred. Suitable differentiated cells include skeletal and cardiac myoblasts, adipocytes, hepatocytes, epithelial cells, fibroblasts, myocytes, myotubes, osteoclasts, osteoblasts, osteocytes, chondrocytes, erythrocytes, leukocytes, thrombocytes, macrophages, neurons, epithelial cells, keratinocytes, melanocytes, vascular and intestinal endothelial cells, hepatocytes, gland cells and kidney cells. Suitable differentiated animal cells may be obtained by any convenient method. In some embodiments, differentiated cells may be produced by differentiating stem cells under suitable conditions.

Each different type of animal cell expresses a different set of genes, leading to differences in the protein, carbohydrate and lipid compositions of each cell type. These differences alter the progression of Maillard reactions and lipid oxidations, and lead to differences in the profile of the flavouring produced by each cell type.

The animal cells may be capable of expansion and proliferation in vitro cell culture. A method described herein may comprise culturing or expanding animal cells in vitro to produce a population of in vitro cultured animal cells.

In other embodiments, the animal cells may be isolated from an animal, such as a meat species as described above. For example, the cells may be primary progenitor cells, embryonic stem cells, induced pluripotent stem cells, mesenchymal stem cells, adult stem cells, transdifferentiated cells, cells from a cultured cell line, such as a commercially available cell line, or immortalized primary cells, for example spontaneously immortalized primary cells, or primary cells immortalized by use of small molecules, genetic modification, or mechanical cues, Immortalized primary cells may be generated by any suitable technique. For example, a population of primary animal cells may be isolated from a source animal and cultured over multiple passages, for example or more, 15 or more, 20 or more, 25 or more or 30 or more passages. Cells within the population that undergo spontaneously immortalization do not enter senescence and continue to proliferate over multiple passages. The spontaneously immortalized primary cells may be isolated and/or stored before use in cell culture.

Suitable techniques for the cell culture of animal cells are well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho W Y et al J Immunol Methods. (2006) 310:40-52, Handbook of Stem Cells (ed. R. Lanza) ISBN: 0124366430) Basic Cell Culture Protocols' by J. Pollard and J. M. Walker (1997), 'Mammalian Cell Culture: Essential Techniques' by A. Doyle and J. B. Griffiths (1997), 'Human Embryonic Stem Cells' by A. Chiu and M. Rao (2003), Stem Cells: From Bench to Bedside' by A. Bongso (2005), Peterson & Loring (2012) Human Stem Cell Manual: A Laboratory Guide Academic Press and 'Human Embryonic Stem Cell Protocols' by K. Turksen (2006). Media and ingredients thereof may be food grade and may be obtained from commercial sources (e.g. Gibco, Roche, Sigma, Europa bioproducts, R&D Systems). Standard mammalian cell culture conditions may be employed for the above culture steps, for example 37° C., 21% Oxygen, 5% Carbon Dioxide. Media is preferably changed every two days and cells allowed to settle by gravity, or optimized frequency and schemes as per culture configuration and/or bioreactor employed.

In some embodiments, the animal cells may be grown in suspension culture to produce the population of in vitro cultured animal cells. The animal cells may be cultured as single cells or as aggregates/organoids (tissues), in a bioreactor that supports high density cell growth, such as a perfusion or fluidic bioreactor, In some embodiments, 3D cell culture may be employed.

Following in vitro cell culture, the animal cells may be harvested. For example, the animal cells may be separated or isolated from the cell culture medium. Suitable methods are well-known in the art. For example, the animal cells may be separated or isolated from the cell culture medium by centrifugation or filtration.

Following harvesting, the animal cells from the in vitro cell culture may be further treated, for example by trypsinization and/or washing.

Following in vitro cell culture, the animal cells may be dried. This may be useful for example, in removing excess water and controlling water activity ($a_w$). Drying the animal cells may allow safer and more efficient flavour extraction as described herein and may also allow further control of Maillard reactions and lipid oxidation during heating, thereby altering the flavour intensity of the meat flavouring.

Water activity is the vapour pressure of water in the aqueous phase of the animal cells divided by the vapour pressure of pure water or salt free water measured at a temperature of 25° C.±1° C. The ratio of water-vapour pressure in the animal cells to the vapour pressure of pure water at the same temperature may be expressed as a figure between 0.0 and 1.0. The water activity of the animal cells may for example be reduced to 0.9 or less, 0.8 or less, 0.7 or less, 0.6 or less, or 0.5 or less. Water activity may be determined by any convenient technique, for example a hygrometric technique (see for example Public Health England 2017).

In some preferred embodiments, the animal cells may be freeze-dried. Freeze-drying the animal cells may reduce premature Maillard reactions and also the loss of aromatic molecules by sublimation. Suitable methods of freeze-drying are well-established in the art.

In other embodiments, the cells may be air- or oven-dried, for example by heating to 40° C. or more 45° C. or more or 50° C. or more.

Following drying, the animal cells may be stored before use in the production of meat flavouring as described herein.

The dried cells or tissues produced by in vitro cell culture methods as described above are heated in fat to produce the meat flavouring.

The fat may be an edible fat. Suitable fats include a non-animal fat, an animal fat, or a mixture of non-animal and animal fat. For example, the edible fat may be a plant fat, such as a vegetable fat.

Suitable fats include fats that are solid at room temperature (~20° C.). Typically, fats that are solid at room temperature are composed of high amounts of saturated fatty acids. Fats may include margarine and butters, such as shea butter, mango butter or cocoa butter.

Suitable fats also include fats that are liquid at room temperature (~20° C.). A fat that is liquid at room temperature may be called an "oil". Typically, fats that are liquid at room temperature are composed of mainly unsaturated fatty acids and are commonly referred to as oils. Suitable oils include an algal oil, a fungal oil, corn oil, olive oil, soy oil, peanut oil, walnut oil, almond oil, sesame oil, cottonseed oil, rapeseed oil, canola oil, safflower oil, sunflower oil, flax seed oil, palm oil, palm kernel oil, coconut oil, babassu oil, wheat germ oil, borage oil, black currant oil, sea-buckhorn oil, macadamia oil, saw palmetto oil, conjugated linoleic oil, arachidonic acid enriched oil, docosahexaenoic acid (DHA) enriched oil, eicosapentaenoic acid (EPA) enriched oil, palm stearic acid, sea-buckhorn berry oil, macadamia oil, saw palmetto oil, or rice bran oil; or other hydrogenated fats.

The fatty acid components of the fat may undergo lipid oxidation and react with Maillard reaction intermediates generated from the animal cells to enhance the flavour and aroma of the flavouring. Fats found to enhance the flavour and aroma of the flavouring include coconut oil and peanut oil.

In some preferred embodiments, the fat may be low in polyphenols, for example less than 50 mg gallic acid equivalent (GAE) per 100 g fat, less than 40 mg GAE/100 g fat, less than 30 mg GAE/100 g fat, less than 20 mg GAE/100 g fat or less than 10 mg GAE/100 g fat. The use of a low-polyphenol fat may for example reduce off-flavours in the flavouring. GAE may be determined by any convenient method. Suitable spectrophotometric techniques are available in the art (see for example Aryal et al 2019).

The fat may be admixed with the dried animal cells before heating to produce the meat flavouring. The volume of fat may depend on the scale of production (research phase, prototype phase, pilot phase, large scale production). For example, the cells may be resuspended in 10 μL, 100 μL or more, 1 mL or more, 100 mL or more, 1 L or more, 10 L or more, 100 L or more, or 1000 L or more, of fat. In some embodiments, 10 μL to 100000 L of fat may be used.

The ratio of animal cells to fat in the admixture may be from $10^5$ animal cells/mL of fat to $10^{10}$ animal cells/mL of fat, for example about $10^5$ animal cells/mL of fat, about $10^6$ animal cells/mL of fat, about $10^7$ animal cells/mL of fat, about $10^8$ animal cells/mL of fat, about $10^9$ animal cells/mL of fat, or about $10^{10}$ animal cells/mL of fat.

Without further treatment, animal cells from in vitro cell culture are not effective in generating meat-specific flavours. In methods of the invention, heating is used as a flavour extraction process to extract meat-specific flavour compounds from the animal cells into the fat.

The animal cells may be heated to 60° C. to 400° C. in the fat. For example, the animal cells may be heated to 60° C. or more, 70° C. or more, 80° C. or more, 90° C. or more, 100° C. or more, 120° C. or more, 130° C. or more, 140° C. or more, 150° C. or more, 200° C. or more, 250° C. or more, 300° C. or more, or 350° C. or more in the fat. In some preferred embodiments, the animal cells may be heated to about 145° C.

The animal cells may be heated for 1 s to 7 days, depending on the temperature employed (higher temperatures allow shorter durations). For example, the animal cells may be heated for 1 min or more, 2 mins or more, 4 mind or more, 6 mins or more, 8 mins or more, 10 mins or more, 60 mins or more, 120 mins or more, 180 mins or more, or 12 hours or more. In some preferred embodiments, the animal cells may be heated for about 10 mins.

The temperature and duration of heating may be adjusted and/or optimised to control the extraction efficiency and degree of Maillard reaction, thus controlling the intensity and type of flavour of the flavouring. For example, the heating temperature and duration may be optimised for each combination of animal cell type, fat and additional ingredients to maintain maximum aroma in the flavouring or provide the desired intensity and type of flavour.

The animal cells and fat may be heated using any convenient technique. Suitable heating devices are readily available in the art. Animal cells and fat may for example be heated as described herein in an airtight vessel to minimize loss of aromatic molecules from the Maillard reaction. Suitable vessels may be capable of withstanding the high internal pressures that may occur during heating.

In addition to dried animal cells and fat, one or more additional ingredients may be added to alter the flavour or aroma of the meat flavouring. For example, the flavour and aroma of meat flavoured oils may be controlled by the addition of food-grade ingredients, thereby altering flavour notes in the flavoured oils. The additional food ingredients may modulate the intensity and note of meat-specific flavours in the flavouring.

A method described herein may comprise admixing one or more food ingredients with the in vitro cultured animal cells and fat. In some embodiments, 10 μg or more of a food ingredient may be admixed per ml of fat. For example, 10 μg to 100 mg of a food ingredient may be admixed per ml of fat, preferably about 10 mg per ml.

The food ingredients may be admixed before, at the same time or after the animal cells and fat are heated.

Suitable food ingredients may include protein ingredients, such as soy protein powder and milk powder; reducing sugars, nucleotides, amino acids, proteins, fatty acids and synthetic flavours.

In some embodiments, the food ingredients admixed with the cells and fat participate in the Maillard reactions that occur when the cells are heated in the fat. A food ingredient may participate in its original form or may degrade or oxidise when subjected to heating to form products that react with Maillard intermediates, proteins, lipids and sugars in or generated by the animal cells. These Maillard reactions generate aromatic compounds that contribute to flavours and aromas in the flavouring.

A meat flavouring produced as described herein may be further mixed with emulsifiers, hydrogels, thickeners, stabilizers and/or other ingredients before use. This may for example improve stability and ease of use.

Following production, a meat flavouring may be stored. For example, a flavouring may be stored in a suitable container in a cool and dry environment.

The invention also provides a meat flavouring produced by a method described herein.

The flavouring may be a meat flavoured edible fat, such as a meat flavoured oil. For example, the flavouring may be a liquid fat or oil; a solid fat; liquid, a semi-solid or solid emulsion with emulsifiers and thickeners; or microencapsulated in hydrogel.

The strength of the flavouring may be calibrated by controlling the dosage. The amount of flavouring added to a foodstuff may be adjusted to the specific application. For example, the flavouring can be diluted with fat, oil, water or other ingredients.

In some embodiments, the strength of flavouring may be further calibrated in a time-dependent or stimulant-dependent manner by the use of biomaterials for immobilization or encapsulation. For example, flavouring may be released in a controlled manner to sustain and maintain sufficient flavour intensities for desired periods of time, for example to impart organoleptic properties. Immobilization or encapsulation may also allow the flavouring to be kept stable until a stimulant is applied (such as a bite), to extend shelf life of the food stuff.

The meat flavouring may be devoid of intact animal cells.

A meat flavouring as described herein may be used as a flavour ingredient to adjust, enhance or alter the flavour or aroma of a foodstuff. For example, the meaty flavour and aroma of a foodstuff intended to be a substitute to meat may be enhanced by adding meat flavoured oils produced by method described herein.

A method of improving the flavour of a food stuff may comprise adding a meat flavouring produced by a method described above to the food stuff.

Suitable foodstuffs include meat substitute products. Meat substitute products are foodstuffs produced from non-animal ingredients, such as plant ingredients, that recapitulate or display the texture, flavour and aroma of meat and are intended to substitute parts of meat, such as but not limited to, muscle and adipose tissue. Meat substitute products may include alternative proteins, meat analogues, plant-based meats, plant-based meat products, cultured meats, cell-based meats, cultivated meats or in vitro meats. A meat substitute may be a muscle or adipose tissue substitute.

Preferred foodstuffs for flavouring as described herein include meat substitute products that lack complex meat aromas and flavours. Examples include plant-based meat substitutes, for example soy protein-, pea protein-, wheat gluten-, tofu-, tempeh-, lentil-, and mycoprotein-meat substitutes.

The flavouring may be added before, during or after the production of the foodstuff.

A meat flavouring may be added to a food stuff as a liquid fat or oil, a solid fat, a liquid, semi-solid or solid emulsion mixed with emulsifiers and thickeners, or a microencapsulated composition.

Meat flavourings as described herein may find wide application in the flavouring of foodstuffs. A meat flavouring may be mixed with a protein isolate prior to heating to form textured proteins by extrusion or Couette cell techniques; or may be added to mixtures of textured proteins and other food ingredients to form ready-to-cook patties, sausages, meat loafs, whole cut meats or other meat substitute products. A meat flavouring produced as described herein may also be used on the surface of a meat substitute product, for example as a marinade or oil coating. This may be useful in imparting flavour during surface cooking methods like grilling, searing and frying In other embodiments, a meat flavouring produced as described herein may be mixed with other ingredients to form fat substitutes; or may also be added as dressing after a foodstuff is cooked.

The meat flavouring may be added to the foodstuff in small quantities. For example, flavouring produced from about $10^9$ animal cells as described herein may be added per kg of foodstuff or foodstuff ingredients.

The invention also provides a food stuff comprising a meat flavouring, such as a meat flavoured oil, produced by a method described above. The foodstuff may be a meat substitute product, such as a plant-based meat product. Meat substitute produces are described above. The foodstuff may further comprise non-animal ingredients, such as plant ingredients. Suitable plant ingredients may include soy protein, pea protein, wheat protein, jackfruit, and edible mushroom mycelium. The foodstuff may be devoid of animal ingredients. The meat flavouring may confer a meat aroma on the foodstuff. For example, the flavouring may confer a meat-specific complex flavour and aroma on the foodstuff Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

EXPERIMENTAL

We developed a method of extracting strong meaty flavours from animal cells produced by in vitro cell culture. Stem cells were isolated from a live animal and cultured to achieve spontaneous immortalization. Cells were washed, air-dried, and heated in plant-based oils to induce extraction of meat-specific complex flavours and aroma. Cells induced to differentiate attained stronger meat-specific flavours and aroma. Aroma and flavour can be further controlled by addition of other food-grade ingredients. We further developed a method of enhancing the flavour of plant-based meat substitutes by incorporating small quantities of animal cell flavour extracts. This imparted meat-specific complex flavours unique to each species that were previously unachievable using plant-based ingredients. The method of flavour extraction from cultured cells and incorporation within plant-based meat substitutes enables the production of better tasting meat alternatives compared to purely plant-based products, and achievable at a much lower cost than existing cell-based meat products given the lower quantity of cells used.

To enable cells to serve as a high-value, low-volume source of meat-specific flavours, the meat-specific flavour and aroma of cells need to be extracted. Our preliminary internal tastes tests have showed that raw cells did not provide meat-specific flavours. The results set out below show that heating small quantities of cultured cells in vegetable fat is able to generate distinctly strong meaty aroma and flavour reminiscent of animal meats and fats of various species. Further, the intensity and note of meat-specific flavours may be controlled by controlling cell fate and by addition of food-grade ingredients. We further demonstrate the utility of the extracted cell essence as flavour ingredients to enhance the flavour of plant-based meat products.

Materials and Methods

Porcine Myoblast Isolation and Culture

Primary porcine satellite cell isolation was performed as described by another study (Ding et al., 2017). Pig muscle tissues were obtained from the extensor carpi radialis of a 6-month old pig (*Sus scrofa*) provided by the National Large Animal Research Facility (SingHealth, Singapore). Freshly collected pig muscles were kept in Dulbecco's modified Eagle medium (DMEM, Life Technologies, USA), low glucose, supplemented with 1% (w/v) penicillin/streptomycin (Life Technologies, USA) on ice between time of sacrifice and cell isolation. Cell isolation was performed within 2 hours after sacrifice of the pig to ensure viability of cells. Tissues were minced finely and dissociated with 2 mg/mL collagenase D (Merck, Singapore) and 1.07 U/mL dispase II (Merck, Singapore) in DMEM with 1% (w/v) penicillin/streptomycin at 37° C. for 1.5 hours with shaking at 200 rpm. The mixture was triturated with pipette once every 15-20 min. After dissociation, the mixture was passed through a sterile fine-mesh strainer to remove large pieces of connective tissue. After centrifuging at 100 g for 5 min, the supernatant was collected and centrifuged at 1000 g for 5 min at 4° C. The cells were washed with 20% foetal bovine serum (FBS, Capricorn Scientific, South America) in DMEM and filtered through a 100 μm cell strainer followed by a 40 μm cell strainer. The cells were then centrifuged at 1000 g for 5 min at 4° C. and incubated with erythrocyte lysis buffer (Merck, Singapore) for 5 min on ice. The cells were than washed with phosphate buffered saline (PBS) twice and the cell pellet reconstituted in myoblast culture media (F10 medium (Life Technologies, USA) with 15% (v/v) FBS, 1% (w/V) penicillin/streptomycin and 10 ng/ml FGF2). Cells were seeded at 70,000 cells per 35 mm collagen coated dish and cultured at 37° C. and 5% (v/v) $CO_2$.

Cells were cultured in myoblast culture media (F10 medium (Life Technologies, USA) with 15% (v/v) FBS, 1% (w/v) penicillin/streptomycin and 10 ng/ml FGF2) in collagen coated dish and cultured at 37° C. and 5% (v/v) $CO_2$.

Medium was changed every two days. Cells were sub-cultured (1:10) when confluency reaches 60-80%.

Chicken Embryonic Fibroblast Isolation and Culture

Primary Chicken embryonic fibroblast cell isolation was performed as described by another study (Intarapat, 2011). Viable chicken eggs were obtained from Asby Singapore Pte Ltd. The egg was transected and the embryo and tissue were separated and kept in Dulbecco's modified Eagle medium (DMEM, Life Technologies, USA), low glucose, supplemented with 1% (w/v) penicillin/streptomycin (Life Technologies). Tissues were minced finely and dissociated with 20 mL Tryple Express with Phenol Red (Gibco, Singapore) at 37° C. for 0.5 hours with shaking at 2200 rpm. After dissociation, the mixture was passed through a sterile fine-mesh strainer. After centrifuging at 1100 rpm for 10 min and incubated with 5 mL ACK lysis buffer (Merck, Singapore) for 5 min on ice. The cells were than washed with phosphate buffered saline (PBS) twice and the cell pellet reconstituted in culture media (DMEM, high glucose with 10% (v/v) FBS, 1% (w/V) penicillin/streptomycin). Cells were seeded at 70,000 cells per 100 mm collagen coated dish and cultured at 37° C. and 5% (v/v) $CO_2$.

Cells were cultured in culture media (DMEM, high glucose with 10% (v/v) FBS, 1% (w/v) penicillin/streptomycin) in collagen coated dish and cultured at 37° C. and 5% (v/v) $CO_2$. Medium was changed every two days. Cells were sub-cultured (1:10) when confluency reaches 60-80%.

C2C12 Culture and Differentiation

Cells were cultured in culture media (DMEM, high glucose with 10% (v/v) FBS, 1% (w/v) penicillin/streptomycin) in collagen coated dish and cultured at 37° C. and 5% (v/v) $CO_2$. Medium was changed every two days. Cells were sub-cultured when confluency reaches 60-80% into 2 experimental sets. The cells were cultured to 90% confluency and the first set was harvested while the differentiation media (DMEM, high glucose with 2% (v/v) Horse Serum (Capricorn Scientific, South America), 1% (w/V) penicillin/streptomycin) was applied to the other set. Differentiation media was changed daily. Upon visual conformation of myotube formation indicating differentiation, the cells were harvested.

Immunofluorescence Staining and Confocal Imaging

Cells were fixed with ice-cold 4% (v/v) paraformaldehyde (PFA in PBS) for 5 mins at room temperature (RT). After washing twice with PBS, samples were permeabilised with 0.3% (v/v) Triton X 100/PBS (PBST) for 30 mins at RT. Fixed and permeabilized cells were blocked with 1% bovine serum albumin (BSA in PBS) for 1 hour at RT. Thereafter, cells were incubated with primary antibodies in PBS overnight at 4° C. Primary antibodies recognizing MyoD (1:200, Proteintech, Singapore, #18943-1) was used. After washing with PBS, cells were incubated with DAPI (1:200, Life Technologies, USA) for 2 hours at RT. After another wash with PBS, cells were immediately imaged with a Zeiss LSM 710 confocal microscope and images processed with Fiji software (Schindelin et al., 2012).

Flavour Extraction from Cells

Cultured cells were trypsinized and washed once with PBS. The cells were centrifuged at 250 g for 3 min at RT and the supernatant was removed, then left to dry in an oven at 50° C. for 45 mins. Once completely dry, 800 μL of coconut oil was added to the dried cells and mixed. The mixture was transferred to a small metal pot and heated on a hot plate at 145° C. for 10 mins to develop and extract meat-specific flavours and aroma. After 2 mins, immediately remove the mixture from the hot plate and allow to cool for 10 mins.

Flavour Control of Cell Essence

Cells were prepared as mentioned above in 3.5, mixed with coconut oil and placed in the metal pot. 0.01 g of milk powder or soy protein powder or both were added to the samples and heated on a hot plate at 145° C. for 10 mins to develop and extract meat-specific flavours and aroma. After 2 mins, immediately remove the mixture from the hot plate and allow to cool for 10 mins.

Sensory Evaluation

Single-blinded taste test was carried out with three volunteers and a sensory evaluation with a hedonic scale (form attached). Volunteers were first asked to smell the samples and record their responses rating the meaty aroma of samples. Volunteers then consumed 100 μL of samples and recorded their responses rating the meaty flavour and overall liking of samples. Volunteers were given water at room temperature to cleanse their palate in between samples.

Preparation of Pork Cutlet Substitute

Plant-based ingredients, including plant-based proteins and natural plant materials, were blended into a dough and seasoning and/cells and/or cell essence added and properly mixed. The dough was coated with all-purpose flour and dipped in egg wash, before coating with panko breadcrumbs. The cutlet was deep fried in sunflower oil until golden brown.

Results

Spontaneously Immortalized Porcine Myoblasts

Primary porcine myoblasts were isolated from a 6-month-old pig and cultured for 20 passages to achieve spontaneous immortalization. Myoblasts expressed MyoD colocalizing with the nucleus. Immortalized porcine myoblasts (IPM) were characterized by immunofluorescence staining for the myoblast marker MyoD (FIG. 1).

Extraction of Meaty Flavours and Aroma from Cells

Figure 2:
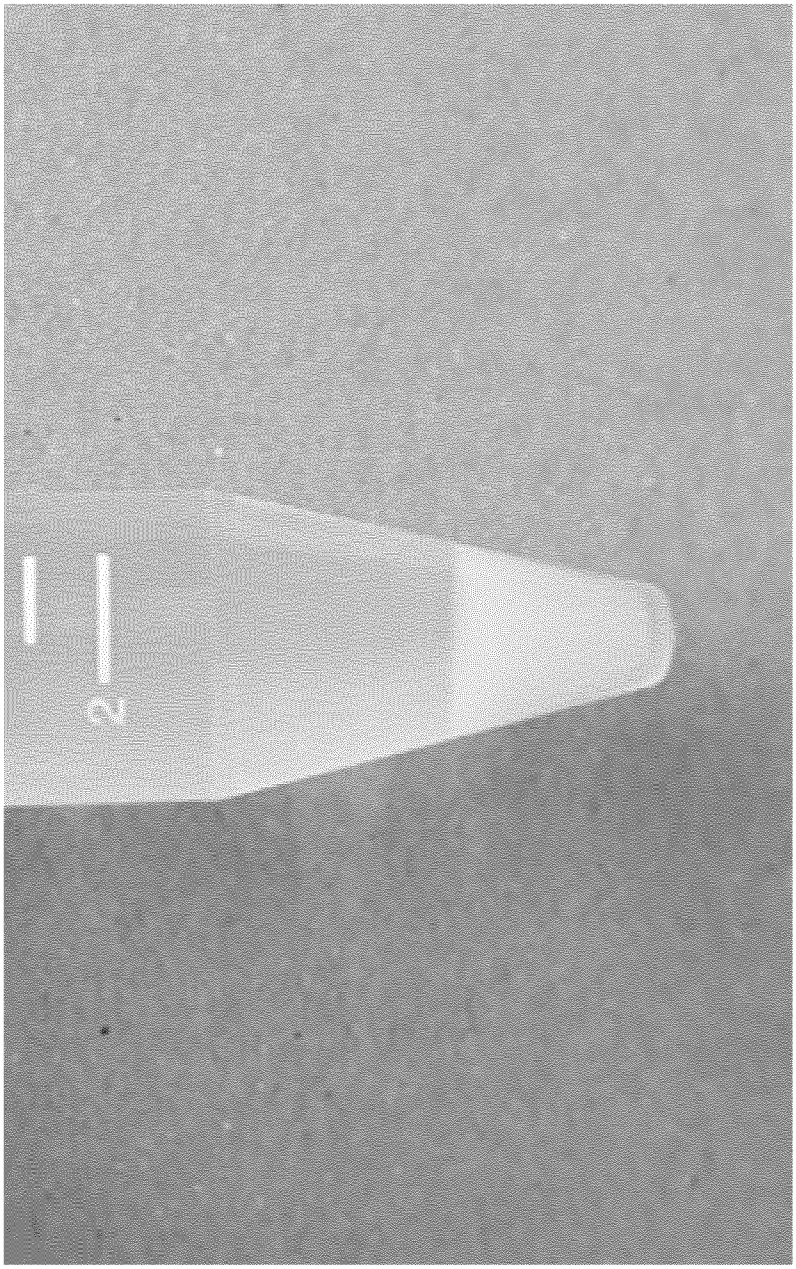
FIG. 2 shows a harvested cell pellet after culture of IPM cells.
Figure 3:
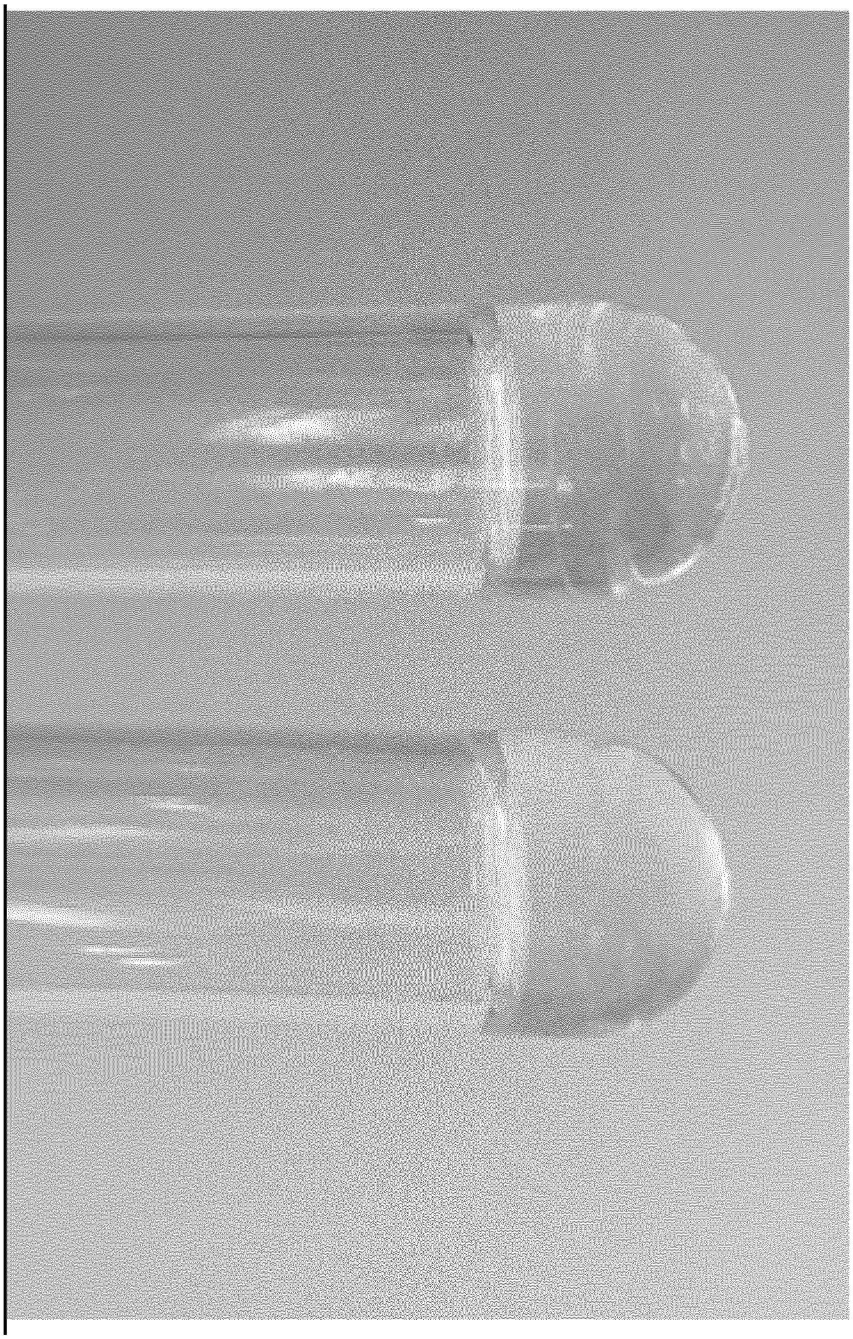
FIG. 3 shows cell essence extracted from porcine myoblasts. (Left) Heated sunflower oil prepared as control. (Right) Extracted cell essence by heating dried porcine myoblasts in sunflower oil.
Figure 4:
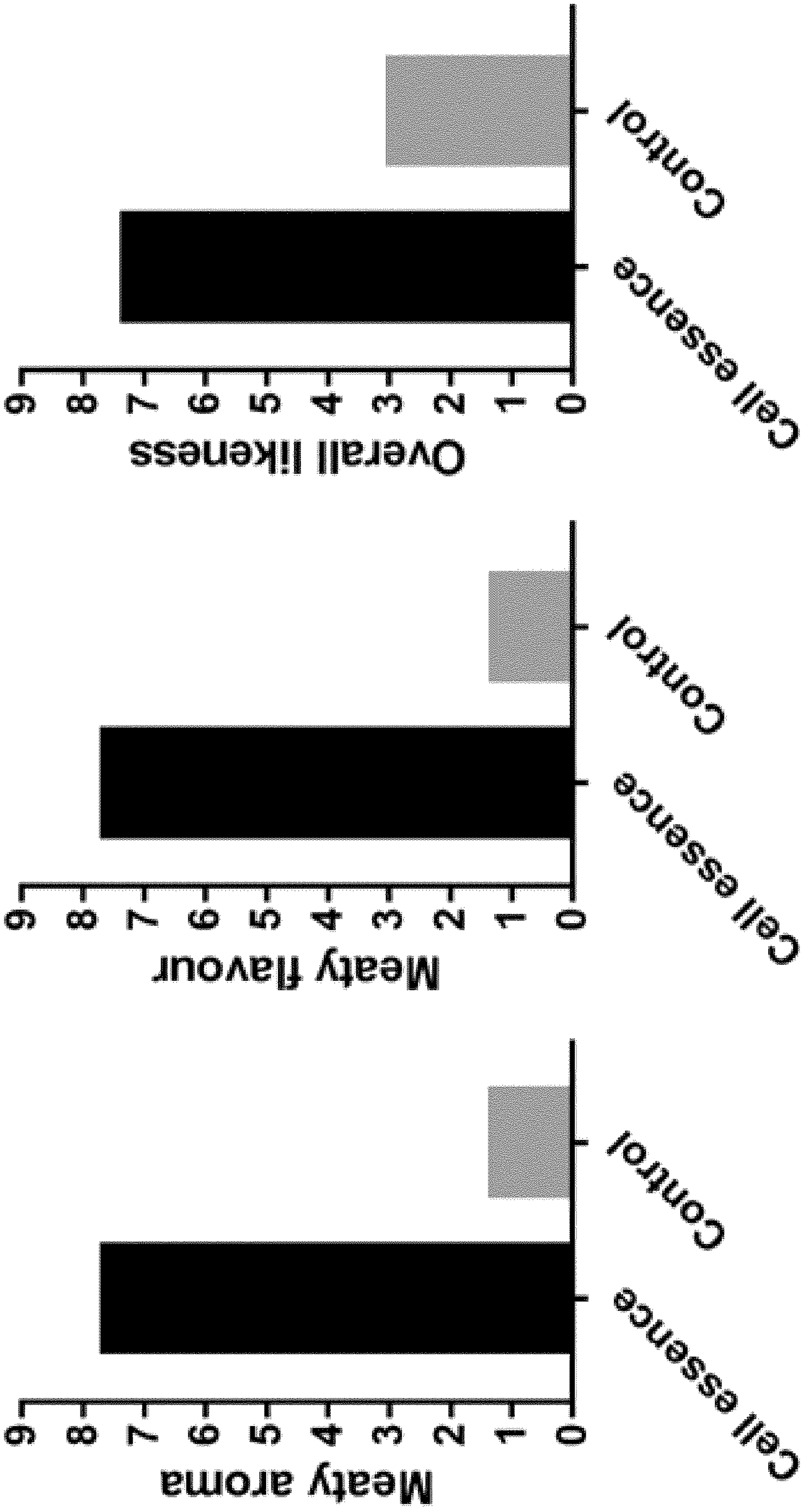
FIG. 4 shows a sensory evaluation of extracted cell essence from IPM using a 9-point hedonic scale to assess development of meaty aroma, flavour, and overall likeness. n=3.
Figure 5:
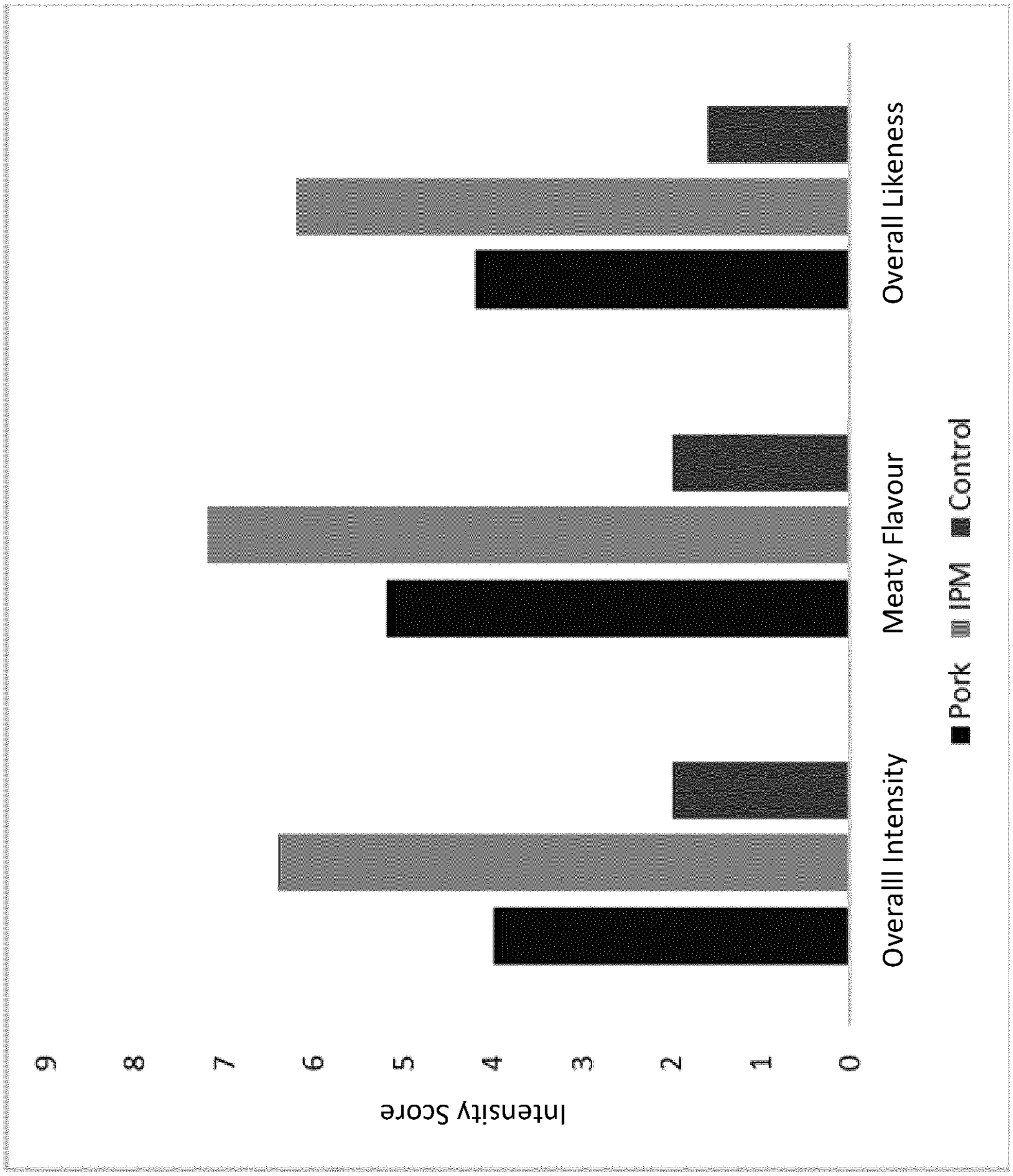
FIG. 5 shows a sensory analysis of cell essence from IPM compared with pork essence similarly extracted from lean pork, with a 9-point hedonic scale to assess development of overall flavour intensity, meaty flavour intensity and overall likeness. n=3.

We have surprisingly found that heating of freeze-dried cells in plant-based oils generates strong meaty aroma which does not present in cultured cells prior to extraction. IPM cells were expanded and harvested to obtain a cell pellet consisting of 20 million cells (FIG. 2). The cell pellet was freeze-dried prior to the flavour extraction process. Thereafter, 500 μL of sunflower oil was added to the dried cell pellet and mixed. After heating to 145° C., meat-like aroma was immediately evident, and the mixture of dried cells and oil developed a yellowish colour (FIG. 3). Taste tests with 3 volunteers revealed significantly strong meaty flavours and aroma in the extracted cell essence compared to the control (FIG. 4). We further compared the flavours generated from the IPM cell essence with flavours from actual meat. The same weight of lean pork muscle meat was freeze-dried, ground and flavours extracted in the same process as the IPM. Taste tests with 3 volunteers surprisingly revealed stronger meaty flavours and aroma in the extracted IPM cell essence compared to the pork essence (FIG. 5). This shows potential for cell essences to perform as a concentrate of meaty flavours to be used in small quantities in alternative meat products to reduce cost and improve scalability.

Sensory Evaluation of Cell Essence Compared with Meat Essence

We further tested the hypothesis that extraction of flavour and aroma from other cells of other species will generate more pronouncedly different flavour and aroma profiles to mimic the flavours of different meat types. Chicken embryonic fibroblasts (CEFs) were isolated from a chicken egg.

Figure 6:
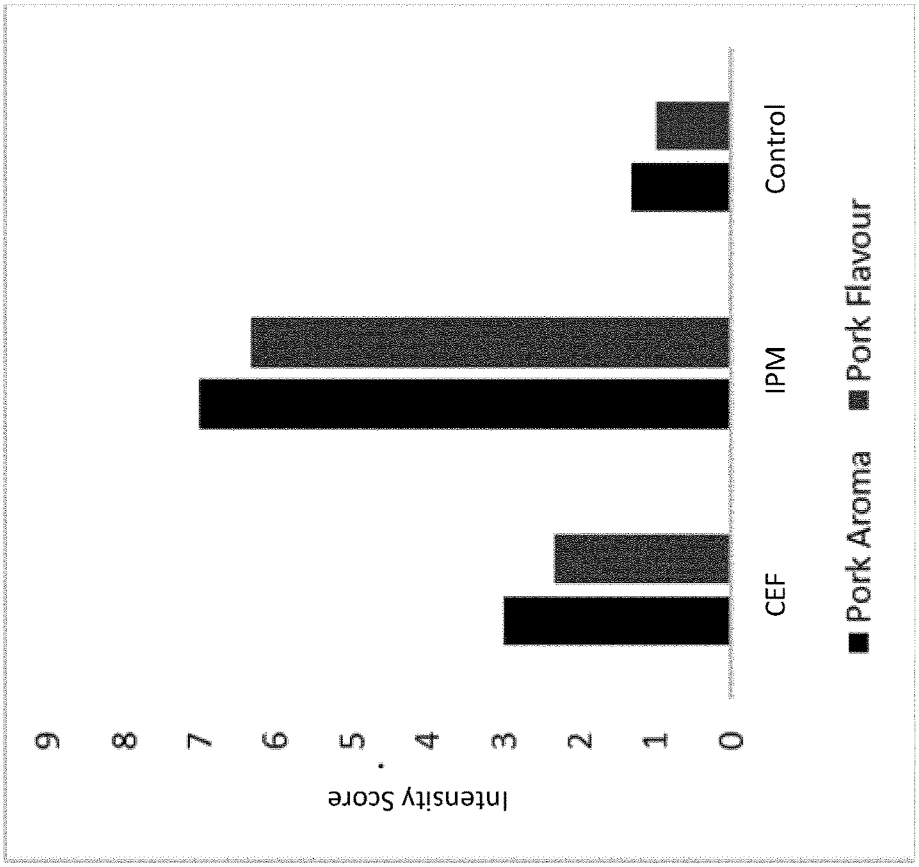
FIG. 6 shows a sensory analysis of extracted cell essences from Chicken Embryonic Fibroblast (CEF) and IPM with a 9-point hedonic scale to assess development of chicken and pork-specific flavours and aromas. n=3.
Figure 6:
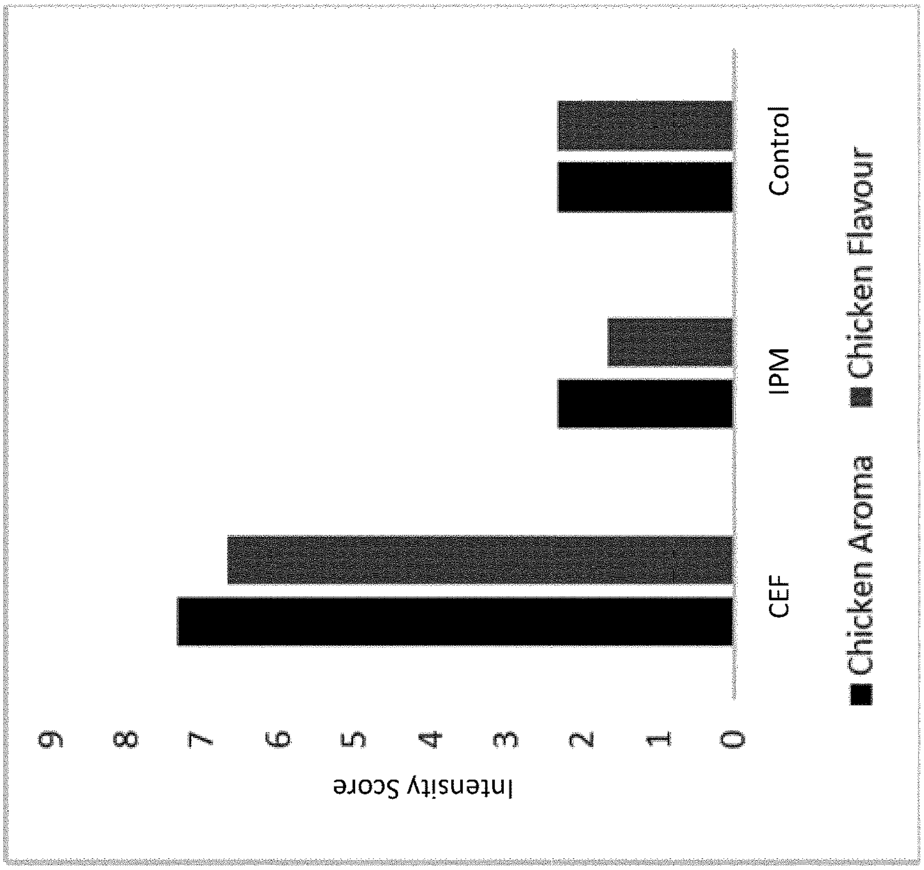

CEFs were expanded, harvested, and processed in the same flavour extraction method as the IPM as described previously. Taste tests with 3 volunteers revealed significantly different species-specific flavour and aroma profiles between the IPM and CEF (FIG. 6).

Sensory Evaluation for Species-Specific Flavours of Cell Essences

Figure 7:
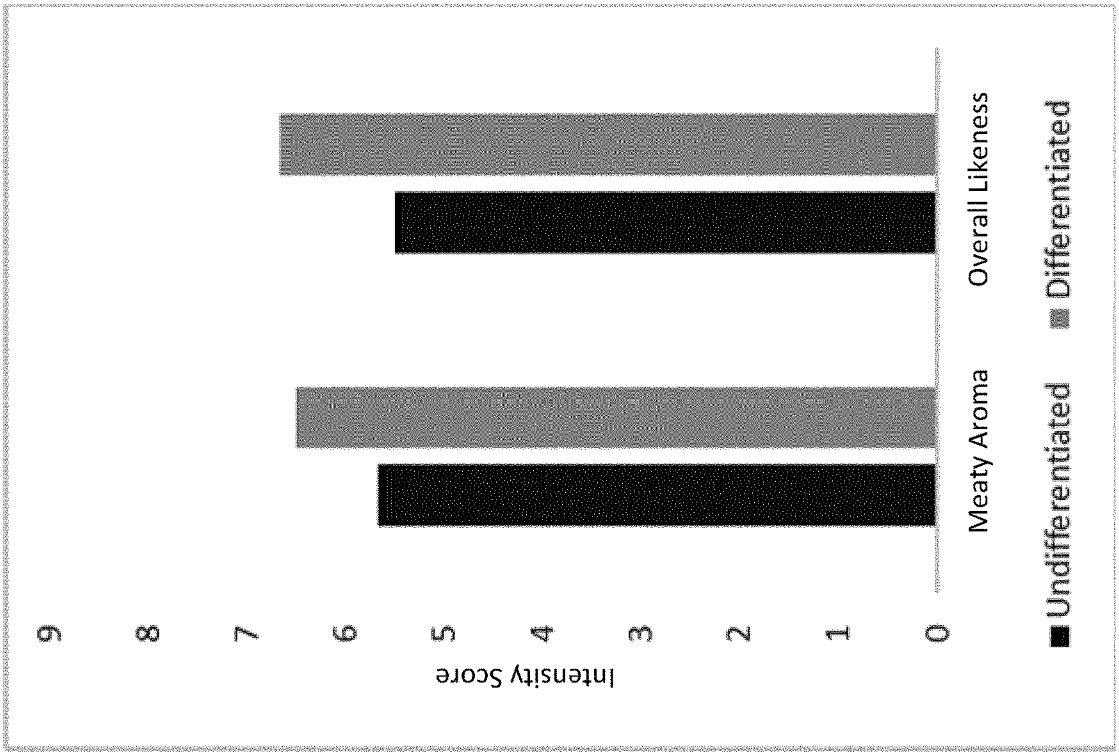
FIG. 7 shows a sensory analysis of differentiated and undifferentiated C2C12 cell essences. Sensory analysis of extracted cell essences from differentiated and undifferentiated C2C12 cells with a 9-point hedonic scale to assess meaty aroma and overall likeness. n=3.

We further sought to control the flavours and aromas generated from the cell essence extraction process. We have found that by controlling cell fate (i.e. differentiation of cells into specific lineages), we are able to control the flavours generated from the cell essence extraction process. To demonstrate this, we used C2C12 cell line and compared the meaty aromas generated from cell essences extracted from differentiated and undifferentiated cells (FIG. 7). Sensory tests (by scent) with 3 volunteers showed stronger meaty aromas and overall likeness in the differentiated cells than in the undifferentiated cells. We thus have demonstrated that different cell linages can generate different flavours after cell essence extraction. Extraction of flavours from other cell types (e.g. adipocytes, hepatocytes, epithelial cells, etc) using the same method disclosed here will generate similar meaty flavour and aroma profiles with subtle differences to mimic the flavours of different types tissue types.

Sensory Evaluation of Differentiated and Undifferentiated C2C12 Cell Essences

Figure 8:
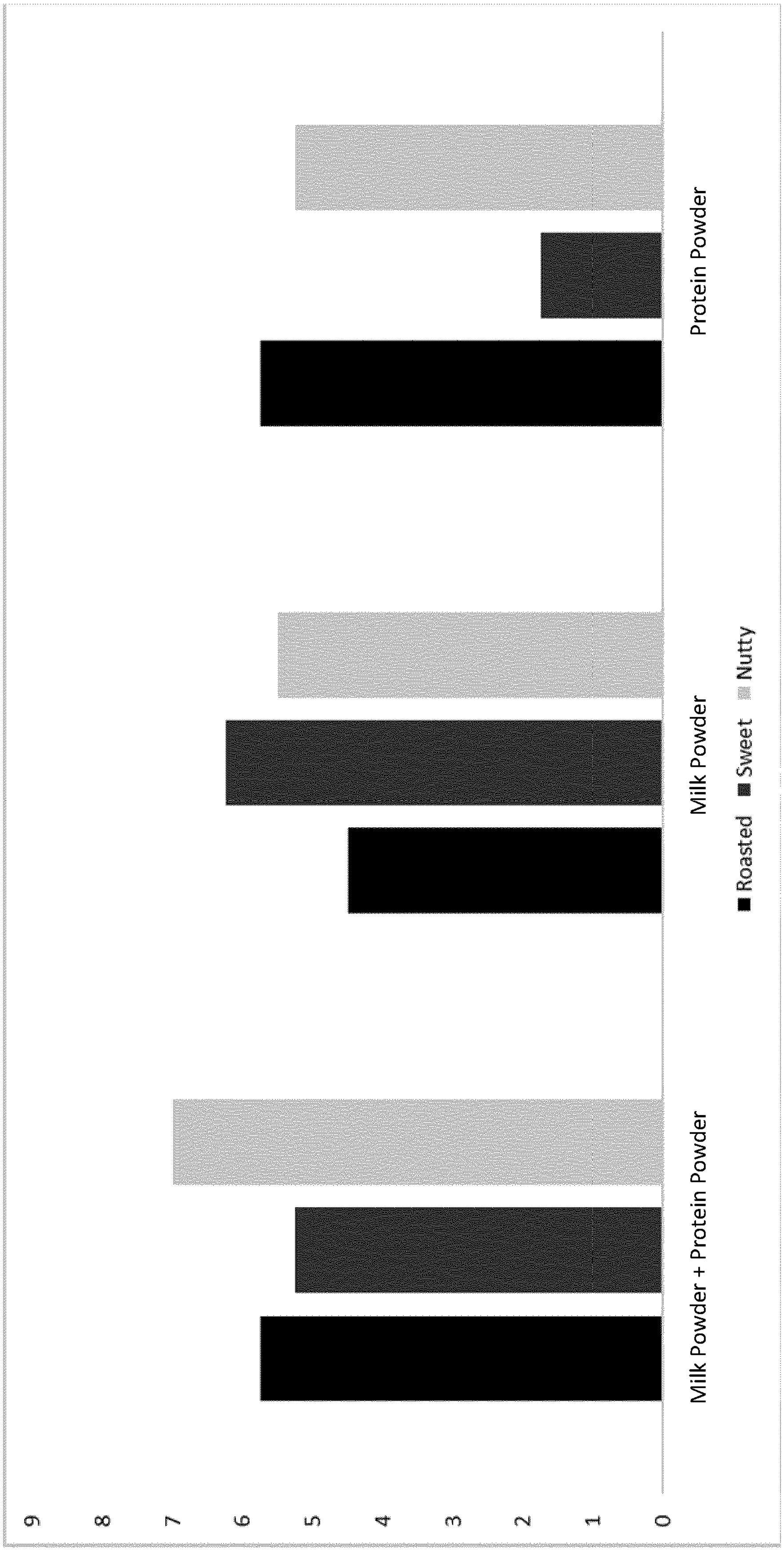
FIG. 8 shows a sensory analysis of extracted IPM cell essences added milk powder or protein powder or both with a 9-point hedonic scale to assess roasted, sweet and nutty notes. n=3.

We have found that the flavours and aromas of cell essences can be controlled by including additional food-grade ingredients in the extraction process. We demonstrated this by adding common high protein ingredients in the extraction mixture (soy protein powder and milk powder). A taste test by 3 volunteers found differences in roasted, sweet and nutty notes when the additives were added (FIG. 8), demonstrating the ability to control flavours in cell essences by addition of other ingredients.

Flavour Enhancement of Plant-Based Meats

Figure 9:
FIG. 9 shows a pork cutlet substitute product produced by a method described herein. (Left) Top view. (Right) Cross-section view showing fibrous texture.
Figure 10:
FIG. 10 shows a meat ball substitute product produced by a method described herein in the context of a noodle soup.
Figure 11:
FIG. 11 shows a meat dumpling substitute product produced by a method described herein.

We demonstrated the utility of the extracted cell essence as a flavouring agent for a wide range of meat substitutes. A pork cutlet, meatball and dumpling substitute made using plant-based ingredients was prepared (FIG. 9-11). Extracted cell essence was added at a ratio of 50 g of plant-based ingredients to 200 μL of cell essence equivalent to $8\times10^6$ of cells. We noted distinct meaty aromas from the pork cutlet substitute product. A cost calculation was performed to assess the commercial feasibility of the extracted cell essence as a flavouring agent based on a few assumptions. Cost of cell culture of derived by assuming a semi-continuous suspension culture process in a 50 L bioreactor with 50% harvesting rate every 2 days similar to the analysis by the Good Food Institute (Specht, 2020). Cells were assumed to have a doubling time of 2 days, achieving maximum cell density of $1\times10^8$ viable cells/mL, undergo 50% media change every day, and media was assumed to be US $376.8/L as cited as the base case of commercial serum-free medium composition by the Good Food Institute. The cost calculation revealed significant reduction in cost of production compared to a conventional 20% cell-based meat (Table 1). The use of extracted cell essence as a flavour enhancer for meat substitutes presents a pragmatic and cost-effective approach for immediate commercialization of meat substitutes incorporating cultured animal cells as ingredients. As the base case medium cost was assumed in this analysis, innovations to reduce medium cost will drive down the cost of production of cell-enhanced products further. The same method may be used to enhance the meat or seafood-specific flavour and aroma of different meat analogs (e.g. beef, chicken, fish, prawn analog, etc.) with minimal cell usage and low cost Tables

TABLE 1

| Ingredient | Cost (USD per kg) | Amount in 20% cell-based product (%) | Amount in cell-enhanced product (kg per kg) |
|---|---|---|---|
| Plant-based ingredients | $ 2.06 | 78% | 97.6% |
| Seasoning | $ 0.78 | 2% | 2% |
| Cells | $7536.00 | 20% | 0% |
| Cell essence | $ 301.44 | 0% | 0.4% |
| Total cost (per kg) | | $1,508.82 | $3.23 |

REFERENCES

1. Aschemann-Witzel, J., Gantriis, R. F., Fraga, P., & Perez-Cueto, F. J. A. (2020). Plant-based food and protein trend from a business perspective: markets, consumers, and the challenges and opportunities in the future. Critical Reviews in Food Science and Nutrition, 1-10. doi: 10.1080/10408398.2020.1793730
2. Ben-Arye, T., & Levenberg, S. (2019). Tissue Engineering for Clean Meat Production. Frontiers in Sustainable Food Systems, 3, 46-46. Retrieved from https://www-.frontiersin.org/article/10.3389/fsufs.2019.00046
3. Ben-Arye, T., Shandalov, Y., Ben-Shaul, S., Landau, S., Zagury, Y., lanovici, I., . . . . Levenberg, S. (2020). Textured soy protein scaffolds enable the generation of three-dimensional bovine skeletal muscle tissue for cell-based meat. Nature Food, 1(4), 210-220. doi:10.1038/s43016-020-0046-5
4. Datar, I., & Betti, M. (2010). Possibilities for an in vitro meat production system. Innovative Food Science and Emerging Technologies, 11(1), 13-22. doi:10.1016/j.if-set.2009.10.007
5. Ding, S., Wang, F., Liu, Y., Li, S., Zhou, G., & Hu, P. (2017). Characterization and isolation of highly purified porcine satellite cells. Cell Death Discovery, 3 (December 2016), 17003-17003. doi:10.1038/cddiscovery.2017.3
6. Intarapat, S 2017, Isolation and characterisation of chick embryonic primordial germ cells, PhD thesis, University College London, London, viewed 22 Jul. 2021, <https://discovery.ucl.ac.uk/id/eprint/1344049>.
7. Ong, S., Choudhury, D., & Naing, M. W. (2020). Cell-based meat: Current ambiguities with nomenclature. Trends in Food Science & Technology, 102, 223-231. doi:https://doi.org/10.1016/j.tifs.2020.02.010
8. Schindelin, J., Arganda-Carreras, I., Frise, E., Kaynig, V., Longair, M., Pietzsch, T, Cardona, A. (2012). Fiji: an open-source platform for biological-image analysis. Nat Meth, 9(7), 676-682. Retrieved from http://dx.doi.org/10.1038/nmeth.2019
9. Specht, L. (2020). An analysis of culture medium costs and production volumes for cell-based meat. The Good Food Institute: Washington, DC, USA,
10. Maughan, Curtis, and Silvana Martini. "Identification and quantification of flavor attributes present in chicken, lamb, pork, beef, and turkey." Journal of food science vol. 77, 2 (2012): S115-21. doi:10.1111/j.1750-3841.2011.02574.x
11. Public Health England (2017). Determination of water activity in food. National Infection Service. Food, Water & Environmental Microbiology Standard Method FNES67 Version 2
12. Aryal et al (2019) Plants 8(4) 96 doi:10.3390/plants8040096

The invention claimed is:

1. A method for producing a meat flavouring comprising;

admixing a population of in vitro cultured non-human animal cells with a fat to produce an admixture consisting of the animal cells and the fat, wherein the admixture consists of from $10^5$ animal cells/mL of fat to $10_{10}$ animal cells/mL of fat, and heating the admixture to a temperature of 60° C. to 400° C., thereby producing the meat flavouring.

2. A method according to claim 1 wherein the admixture is heated for 1 second to 7 days.

3. A method according to claim 1 wherein the fat is a solid fat.

4. A method according to claim 1 wherein the fat is an oil.

5. A method according to claim 4 wherein the fat is an algal oil, a fungal oil, corn oil, olive oil, soy oil, peanut oil, walnut oil, almond oil, sesame oil, cottonseed oil, rapeseed oil, canola oil, safflower oil, sunflower oil, flax seed oil, palm oil, palm kernel oil, coconut oil, babassu oil, wheat germ oil, borage oil, black currant oil, sea-buckhorn oil, macadamia oil, saw palmetto oil,, sea-buckhorn berry oil, macadamia oil, saw palmetto oil, or rice bran oil, or other hydrogenated fats.

6. A method according to claim 1 wherein the animal cells are differentiated or undifferentiated cells.

7. A method according to claim 6 wherein the animal cells are skeletal and cardiac myoblasts, myocytes, myotubes, fibroblasts, osteoclasts, osteoblasts, osteocytes, chondrocytes, erythrocytes, leukocytes, thrombocytes, macrophages, adipocytes, neurons, epithelial cells, keratinocytes, melanocytes, vascular and intestinal endothelial cells, hepatocytes, gland cells or kidney cells.

8. A method according to claim 1 wherein the animal cells are from a livestock, poultry or aquatic species.

9. A method according to claim 1 wherein the method comprises providing a population of in vitro cultured non-human animal cells.

10. A method according to claim 9 wherein the population of in vitro cultured non-human animal cells is provided by a method comprising;

culturing animal cells in vitro to produce a population of in vitro cultured animal cells and drying said population.

* * * * *